(12) United States Patent
Greene et al.

(10) Patent No.: US 8,748,167 B2
(45) Date of Patent: Jun. 10, 2014

(54) COMPACT AIR PURIFIER

(75) Inventors: Wesley O. Greene, Asheville, NC (US); Brian D. Summers, Biltmore Lake, NC (US); Roy D. Crowninshield, Asheville, NC (US)

(73) Assignee: SGBlue, Inc., Asheville, NC (US)

( * ) Notice: Subject to any disclaimer, the term of this patent is extended or adjusted under 35 U.S.C. 154(b) by 922 days.

(21) Appl. No.: 12/896,216

(22) Filed: Oct. 1, 2010

(65) Prior Publication Data

US 2011/0318817 A1    Dec. 29, 2011

Related U.S. Application Data

(60) Provisional application No. 61/358,643, filed on Jun. 25, 2010.

(51) Int. Cl.
*A62D 3/02* (2007.01)
*B01D 53/74* (2006.01)
*B01D 53/86* (2006.01)
*A61L 9/04* (2006.01)
*B01D 47/02* (2006.01)
*F24F 3/16* (2006.01)

(52) U.S. Cl.
CPC .............. *A61L 9/044* (2013.01); *B01D 47/027* (2013.01); *B01D 2221/02* (2013.01); *B01D 2259/4508* (2013.01); *B01D 2259/45* (2013.01); *F24F 3/16* (2013.01)
USPC ..................... 435/299.1; 435/262.5; 422/121; 422/122; 422/123; 422/124

(58) Field of Classification Search
CPC ........ A61L 9/044; B01D 53/38; B01D 53/84; B01D 47/027; B01D 2221/02; B01D 2247/14; B01D 2251/95; B01D 2255/804; B01D 2258/06; B01D 2259/45; B01D 2259/4508; F24F 3/16; F24F 2003/1617
USPC ................. 422/120, 121, 122, 123, 124, 125; 435/262.5, 299.1; D23/356, 364; 261/30, 104, 106, 107; 128/203.27
See application file for complete search history.

(56) References Cited

U.S. PATENT DOCUMENTS

| | | | | |
|---|---|---|---|---|
| 1,702,804 | A | * | 2/1929 | Winslow ......................... 96/321 |
| 1,955,518 | A | * | 4/1934 | Sherwood ....................... 261/91 |
| 4,032,407 | A | * | 6/1977 | Scott et al. .................... 435/177 |
| 4,689,302 | A | | 8/1987 | Goldberg et al. |
| 4,839,014 | A | * | 6/1989 | Park et al. ..................... 204/265 |
| 6,248,155 | B1 | * | 6/2001 | Seaman ......................... 95/211 |
| 6,916,630 | B2 | | 7/2005 | Sofer |
| D633,996 | S | * | 3/2011 | Laut et al. .................... D23/364 |

(Continued)

OTHER PUBLICATIONS

Xu, Derwent abs of CN 2899905, May 16, 2007.*

(Continued)

*Primary Examiner* — Michael Marcheschi
*Assistant Examiner* — Shanta G Doe
(74) *Attorney, Agent, or Firm* — Nexsen Pruet, LLC

(57) ABSTRACT

An air purifier with a tub capable of containing a liquid. Reactor plates are in the tub wherein the reactor plates provide a curvilinear path for air flow with abrupt directional change. A pump is situated to distribute the liquid onto the reactor plates to form a moist surface. An air inlet brings contaminated air into contact with biocatalyst on the moist surface thereby forming purified air. An air outlet discharges said purified air from the air purifier.

27 Claims, 7 Drawing Sheets

(56) References Cited

U.S. PATENT DOCUMENTS

2006/0096461 A1* 5/2006 Kim et al. .................. 96/283
2007/0004023 A1* 1/2007 Trachtenberg ............. 435/266
2007/0278702 A1* 12/2007 French et al. ............. 261/79.2

OTHER PUBLICATIONS

Kim Jae Jung, International Search Report and Written Opinion, PCT/US2011/04514, Jan. 20, 2012.

* cited by examiner

COMPACT AIR PURIFIER

CROSS-REFERENCE TO RELATED APPLICATIONS

The present application claims priority to U.S. Provisional Appl. No. 61/358,643 filed Jun. 25, 2010 which is incorporated herein by reference.

BACKGROUND OF THE INVENTION

The present invention is related to a compact air purifier which is ideally suited for residential applications. More specifically, the present invention is related to an improved configuration for a compact bioreactor for purifying air passing there through.

Air purifiers are typically designed with a flow-through chamber wherein biocatalyst are on the interior surfaces of the bioreactor. The biocatalyst converts contaminants flowing in a medium, preferably water, into another material. The conversion can be by oxidation or other methods wherein the contaminant is preferably converted from a toxic, or undesirable, material into a non-toxic or desirable material.

Due to the desire for a high surface area the art has evolved towards spiral reactors as described in U.S. Pat. No. 6,916,630 to Sofer, or U.S. Pat. No. 4,689,302 to Goldberg et al. both of which are incorporated herein by reference. Those of skill in the art have optimized the spiral design to the extent that they are highly efficient and this configuration now represents what is considered to be the state of the art in flow through reactor design.

Unfortunately, spiral designs have a limited volume capability and are limited by slip-streams in the flow which limit effective interactions between contaminant and catalyst. Other designs, which afford high volume, virtually always have limited functionality with regards to the amount of material converted in the reactor.

Those of skill in the art have therefore been limited to either an efficient reactor or a high volume reactor with the only option there between being multiple parallel reactors. None of these options are conducive to a compact design as would be desired in residential applications.

The present invention provides a reactor design which affords high volume throughput in a compact design with excellent reactivity between biocatalyst and contaminant.

BRIEF SUMMARY OF THE INVENTION

It is an object of the invention to provide an air purifier which is compact and suitable for residential applications.

It is another object of the invention to provide a compact bioreactor.

A particular feature of the present invention is the efficiency of the system with regards to the volume of air which can be purified in a compact design.

These and other embodiments, as will be realized, are provided in an air purifier. The air purifier has a tub capable of containing a liquid. Flow restrictor walls are in the tub. An outer arcuate reactor plate is in the tub wherein the outer arcuate reactor plate comprises a first truncated cylinder with a first truncation and a second truncation wherein the first truncation is an open truncation and the second truncation is attached to the flow restrictor walls. An intermediate arcuate reactor plate is interior to the outer arcuate reactor plate wherein the intermediate arcuate reactor plate comprises a second truncated cylinder. An interior arcuate reactor plate is interior to the intermediate arcuate reactor plate wherein the interior arcuate reactor plate comprises a third truncated cylinder comprising a third truncation and a fourth truncation wherein the third truncation is an open truncation and the fourth truncation is attached to the flow restrictor walls. A pump is situated to draw liquid containing a biocatalyst from a region formed by the interior arcuate reactor plate and the flow restrictor walls for distribution onto a cap. The cap is on the tub wherein the cap comprises liquid voids and liquid passes through the liquid voids and wets at least one of the outer arcuate reactor plate, the intermediate arcuate reactor plate, the interior arcuate reactor plate or the flow restrictor walls to form a moist surface. An air inlet brings contaminated air into contact with biocatalyst on at least one moist surface thereby forming purified air. An air outlet discharges purified air from the air purifier.

Yet another embodiment is provided in a method of purifying air. The method includes providing an air purifier comprising a tub capable of containing a liquid; flow restrictor walls in the tub; an outer arcuate reactor plate in the tub wherein the outer arcuate reactor plate comprises a first truncated cylinder with a first truncation and a second truncation wherein the first truncation is an open truncation and the second truncation is attached to the flow restrictor walls an intermediate arcuate reactor plate interior to the outer arcuate reactor plate wherein the intermediate arcuate reactor plate comprises a second truncated cylinder; an interior arcuate reactor plate interior to the intermediate arcuate reactor plate wherein the interior arcuate reactor plate comprises a third truncated cylinder comprising a third truncation and a fourth truncation wherein the third truncation is an open truncation and the fourth truncation is attached to the flow restrictor walls a pump situated to draw liquid from a region formed by the interior arcuate reactor plate and the flow restrictor walls for distribution onto a cap; the cap is on the tub wherein the cap comprises liquid voids wherein the liquid passes through the liquid voids and wets at least one of the outer arcuate reactor plate, the intermediate arcuate reactor plate or the interior arcuate reactor plate; an air inlet brings contaminated air into contact with moist biocatalyst on at least one moist surface thereby forming purified air; and an air outlet for discharging purified air from the air purifier. The method also includes providing a biocatalyst in a liquid and inserting the liquid in said tub. Contaminated air is drawn into the air purifier wherein the contaminant reacts with the biocatalyst thereby forming an inert material and the purified air is exhausted from the air purifier.

Yet another embodiment is provided in an improved air purifier. The air purifier has a tub capable of containing a liquid. Reactor plates are in the tub wherein the reactor plates provide a curvilinear path for air flow with abrupt directional change. A pump is situated to distribute the liquid onto the reactor plates to form a moist surface. An air inlet brings contaminated air into contact with biocatalyst on the moist surface thereby forming purified air. An air outlet discharges said purified air from the air purifier.

DETAILED DESCRIPTION

The present invention is related to a compact air purifier for removing contaminants from air. More specifically, the present invention is related to a compact air purifier which relies on a bioreactor adhered to moist interior surfaces thereof. The purifier is extremely efficient at purifying air flowing there through and the efficiency renders the purifier extremely useful for use in small environments such as a home.

The invention will be described with reference to the figures which are an integral component of the instant invention. Throughout the figures similar elements will be numbered accordingly.

Figure 1:
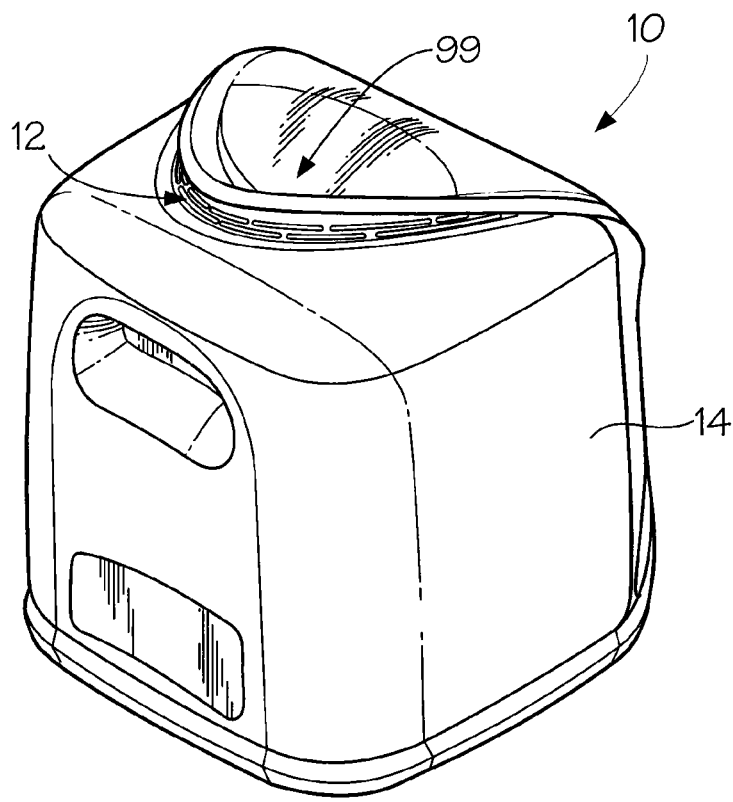
FIG. 1 is a front perspective schematic view of an embodiment of the invention.

An embodiment of the invention is illustrated in schematic perspective view in FIG. 1. In FIG. 1, the air purifier is generally represented at 10. The air purifier has an external casing, 14, which encases the inner workings which will be described further herein. An air grid, 12, allows purified air to exit the casing. Openings 98 and 99 allow contaminated air to enter the casing. It would be readily apparent that the air grid can allow air to enter the casing and the air can then exit the openings. Single or multiple air inlet and exit locations may be utilized. The design of the casing is dictated, in part, by aesthetics with the understanding that it must be of such a size and shape to contain the inner workings and provide for the appropriate number of air grids.

Figure 2:
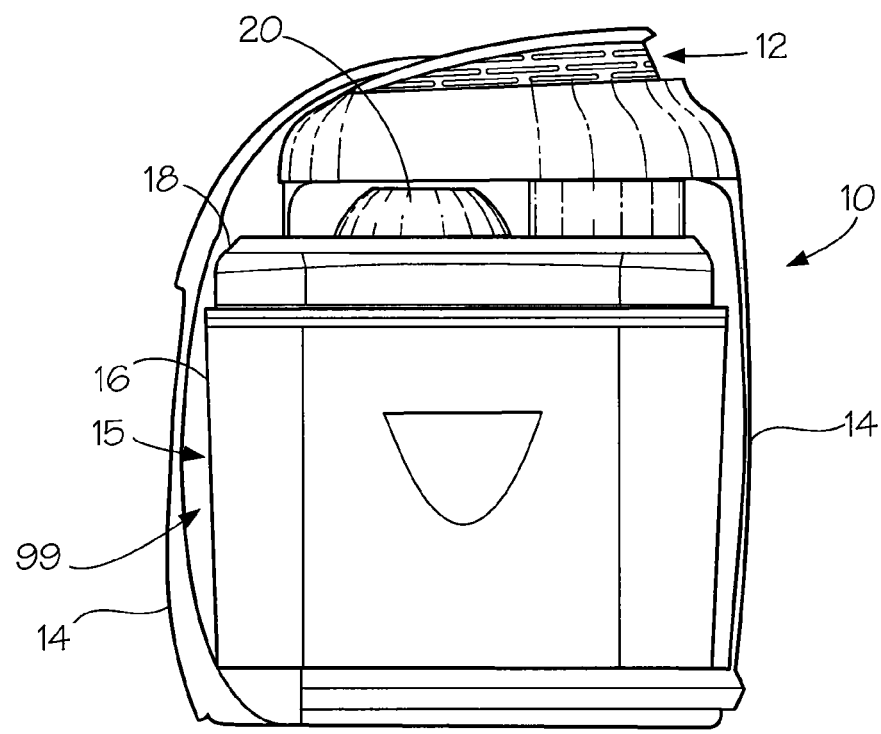
FIG. 2 is a side schematic view of an embodiment of the invention in partial cut-away view.

A partial cut-away side schematic view is provided in FIG. 2. In FIG. 2, the inner workings, 15, comprise a lower tub, 16, and a cap, 18, which is, preferably removably, attached to the top of the tub. A deflector, 20, which will be described in more detail herein, is on the cap.

Figure 3:
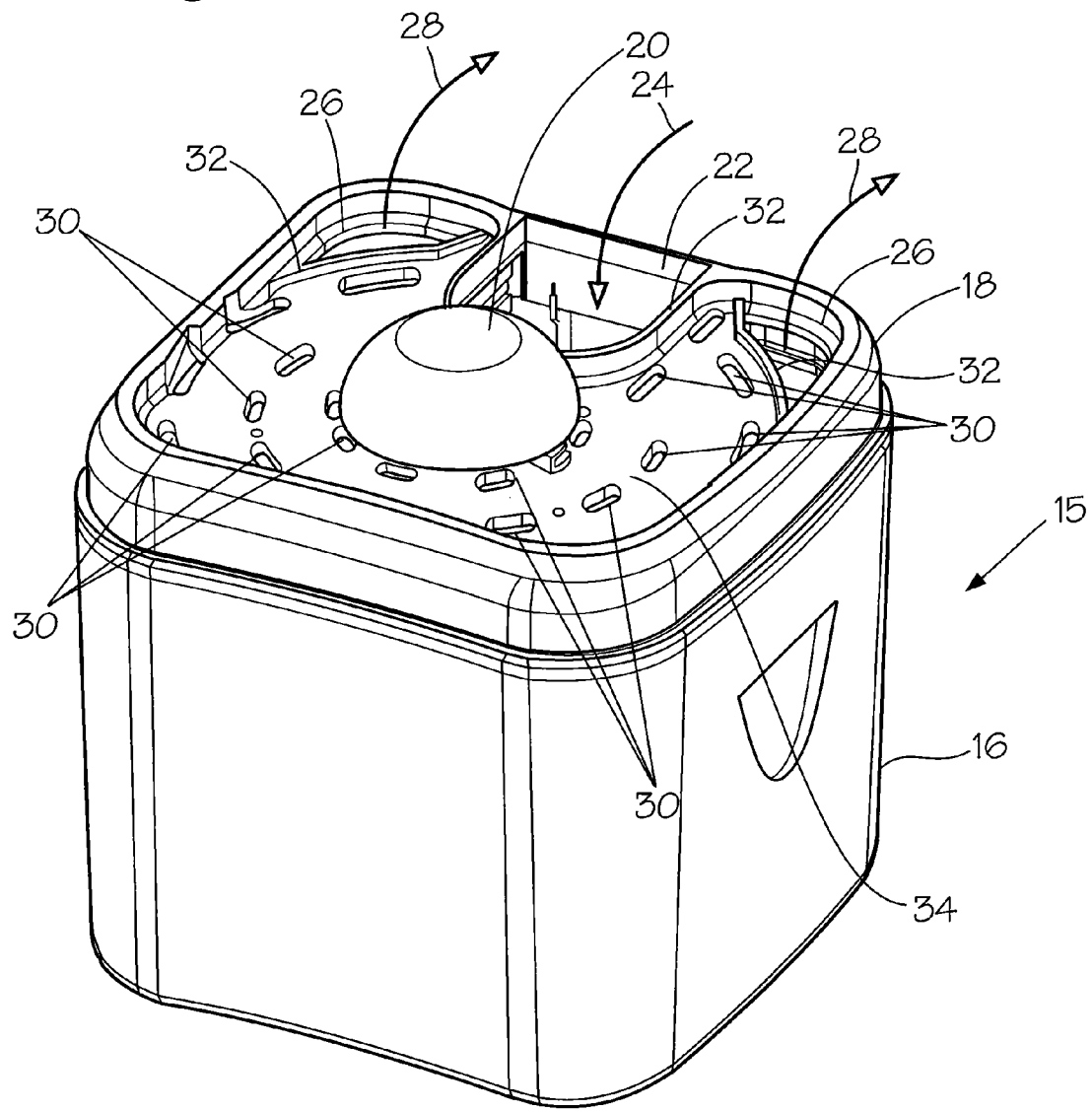
FIG. 3 is a top perspective schematic view of an embodiment of the invention with the external case removed.

The inner workings are illustrated in isolated perspective schematic view in FIG. 3. In FIG. 3, the cap, 18, is shown to contain a plurality of voids there through. At least one air inlet void, 22, allows contaminated air to flow into the inner workings as illustrated by arrow 24. At least one air outlet void, 26, allows purified air to flow out of the inner workings as illustrated by arrows, 28. In the embodiment shown there is a single air inlet void with two air outlet voids. This is a preferred embodiment but the invention is not limited thereto. The number of air inlet voids and air outlet voids can be altered with the proviso that the total volume of air passing into the inner workings must be allowed to pass out of the inner workings. A series of liquid voids, 30, are dispersed over the cap, 18, in a pattern which will be more apparent after further discussion. Dams, 32, form a reservoir over that portion of the cap with water voids thereby insuring that liquid which exits from under the deflector, 20, spreads across the face, 34, of the cap but the liquid is restricted from entering an air inlet void or air outlet void unless the pool height is higher than the dams which is not desirable.

Figure 4:
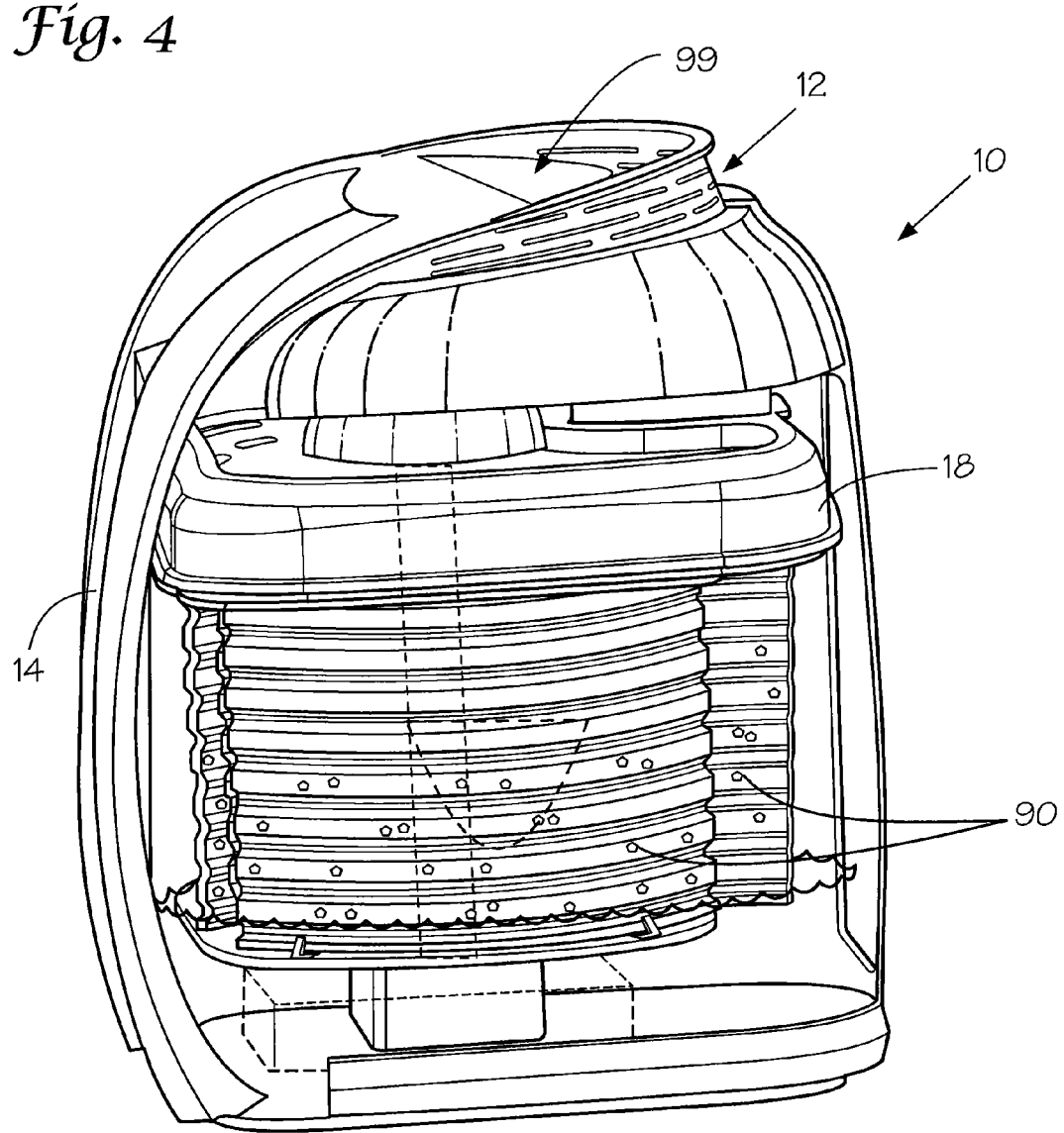
FIG. 4 is a side schematic view of an embodiment of the invention is partial cut-away view.
Figure 5:
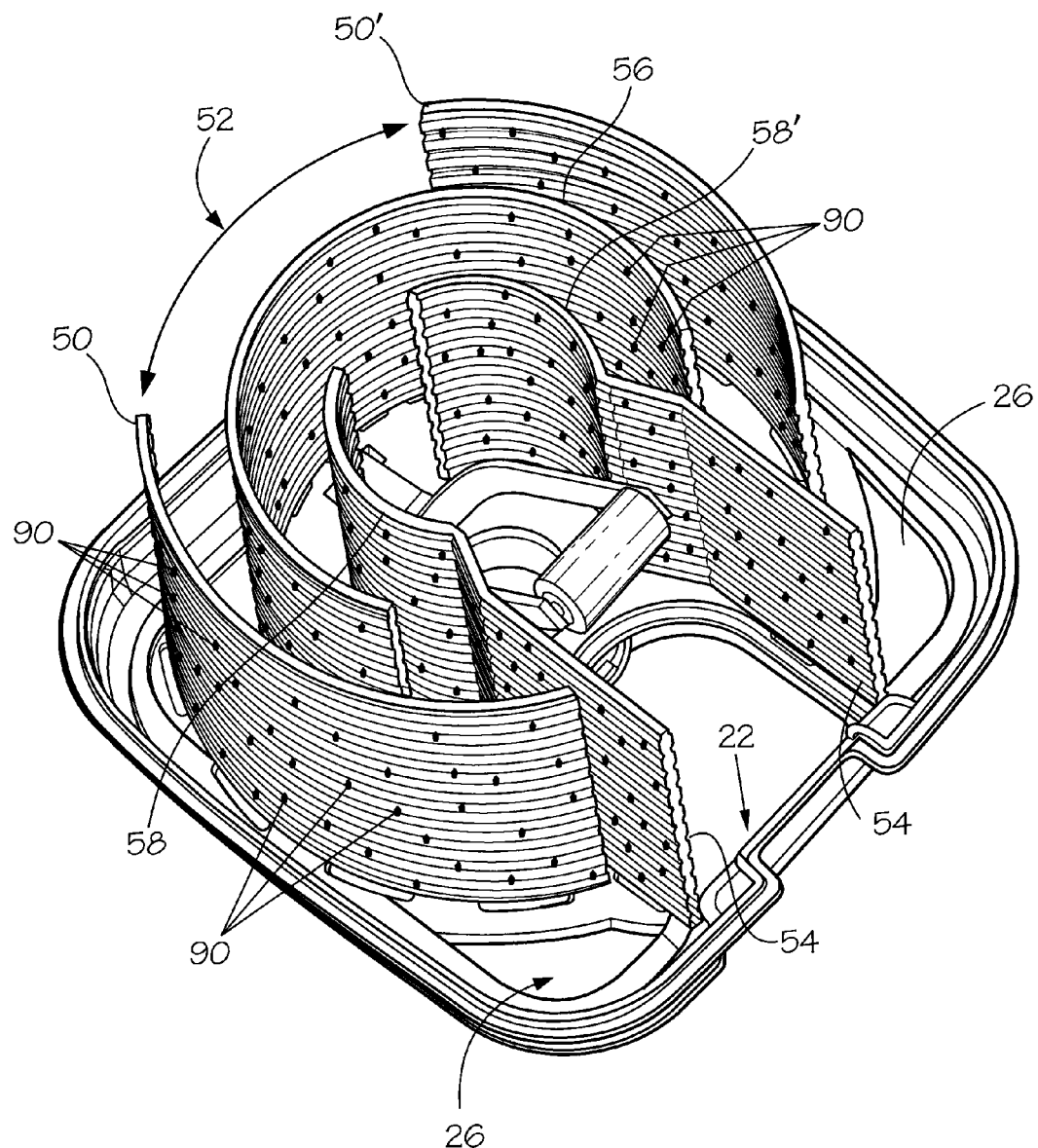
FIG. 5 is a bottom perspective schematic partial view of an embodiment of the invention
Figure 6:
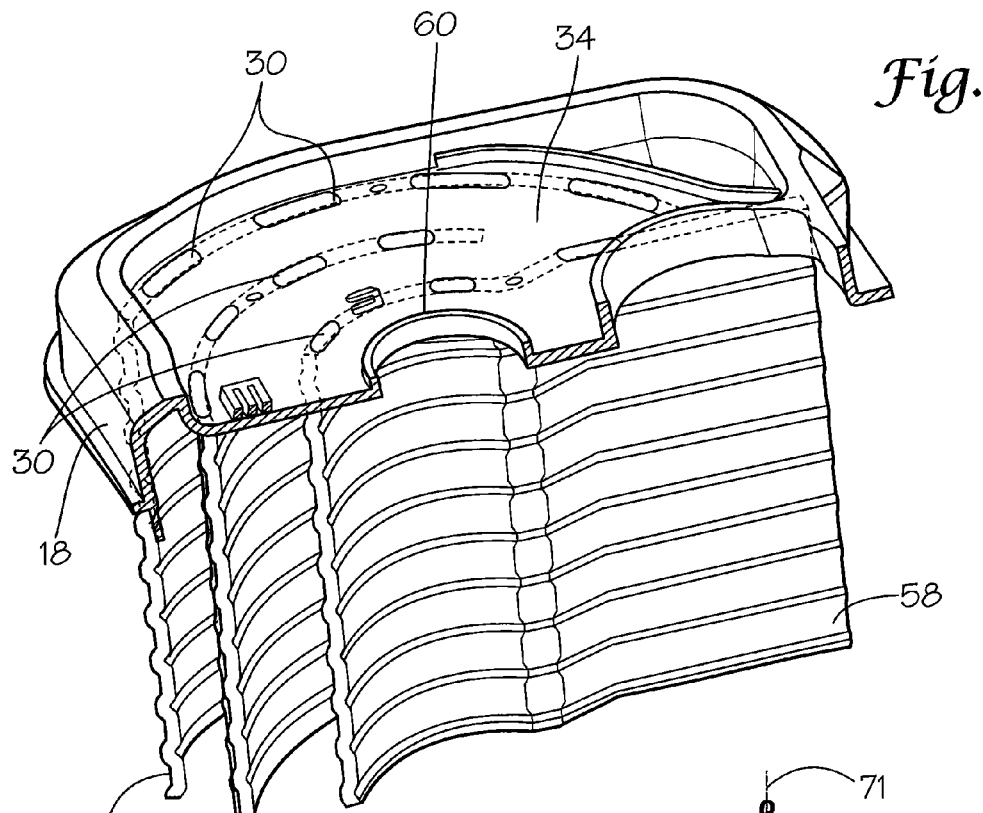
FIG. 6 is a top perspective schematic partial view of an embodiment of the invention.
Figure 7:
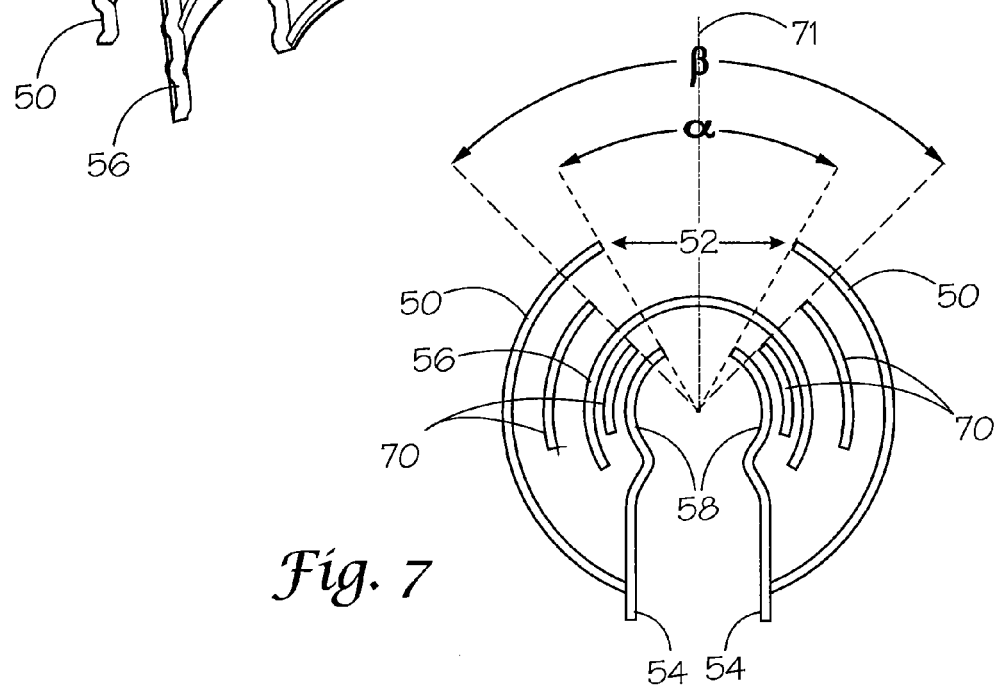
FIG. 7 is a top schematic partial view of an embodiment of the invention.
Figure 8:
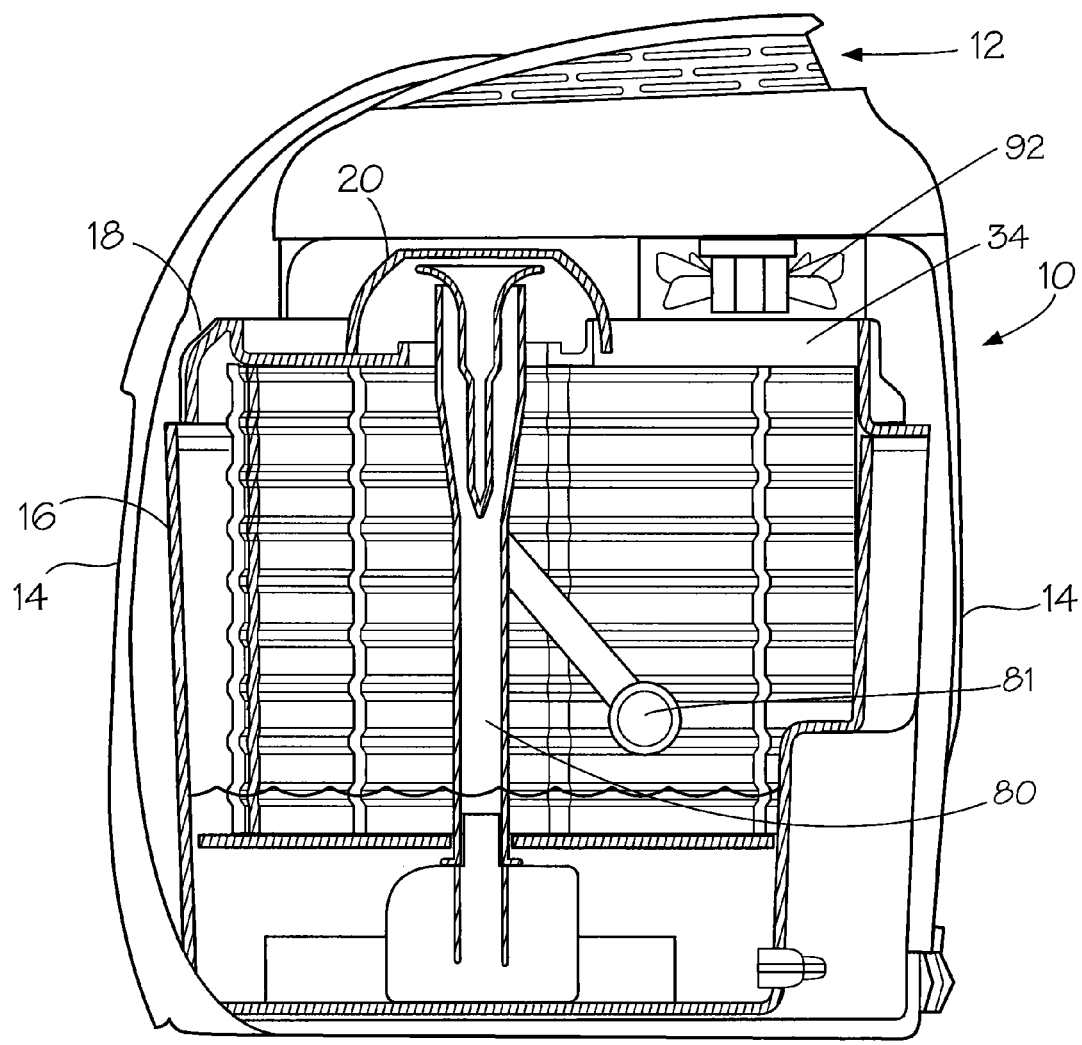
FIG. 8 is a side schematic view of an embodiment of the invention is partial cut-away view.
Figure 9:
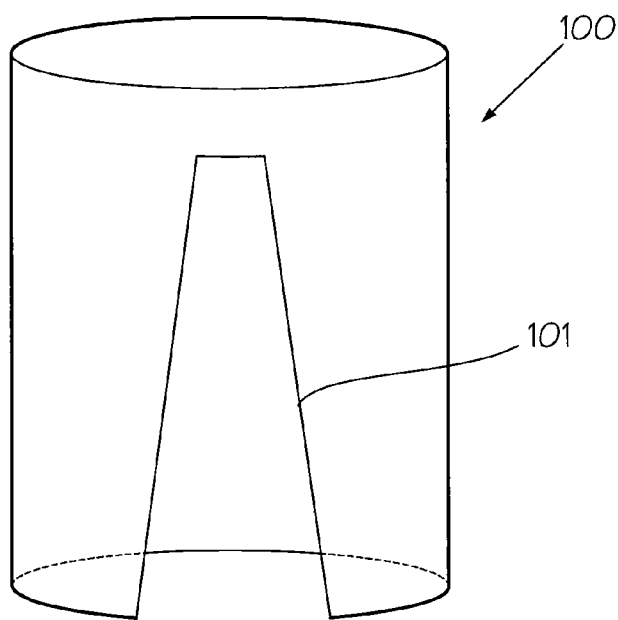
FIG. 9 is a perspective view of an embodiment of the invention.

Arcuate reactor plates are disposed within the tub. Their orientation relative to the water voids will be described with reference to FIGS. 4-6. FIG. 4 is a schematic side view shown in partial cut-away. FIG. 5 is a schematic isolated bottom view of the cap and arcuate reactor plates with the tub removed for clarity. FIG. 6 is a schematic isolated view of the cap and arcuate reactor plates looking from the top with the reactor plates in partial cutaway.

The reactor plates, taken together, form a preferably symmetric tortuous path for flow of air and water in a counter flowing relationship. The air which enters in opening 22 and later exits through opening 26 flows through gradually curved paths interrupted by abrupt directional changes. The inner reactor plate, 58, and the intermediate reactor plate, 56, forming the initial gradually curved airflow passages provide for a high surface area bioactive interface to the immediately adjacent portion of the curvilinear airstream. These portions of the airstream adjacent to the reactor plates are thus cleansed of airborne contaminants. The inner reactor plate, 58, and intermediate reactor plate, 56, for example form a geometry that requires the airflow to abruptly change direction and to reverse the curvilinear air flow. This abrupt change in direction produces local airflow turbulence resulting in a remixing of air and airborne contaminants. For the purposes of the instant application an abrupt change in direction is at least 90° relative to the direction of flow. The remixed contaminated air then flows through the gradually curved path formed by outer reactor plate, 50, and intermediate reactor plate, 56, which provides for a high surface area bioactive interface to the immediately adjacent portion of the curvilinear airstream. These portions of the airstream adjacent to the reactor plates are thus cleansed of airborne contaminate. The reversal of airflow and the remixing of the air and contaminants results in a two stage bioreactor. A biocatalyst, 90, on the walls of the reactor plates react with the contaminants thereby purifying the air as it is circulated through the tortuous path.

The reactor plates, taken together, form a preferably symmetric tortuous path for flow of air and water in a counter flowing relationship. This counter flowing design allows for the efficient flow of air within a compact space saving design and with quiet operation. These features are of unique importance in residential air purifiers.

With reference to FIG. 5, the arcuate reactor plates are represented as truncated cylinders. The outer reactor plate, 50, is a twice truncated cylinder with two half circles, 50 and 50'. A first truncation, 52, forms a flow passage as will be more fully understood and the second truncation is sealed by flow restrictor walls, 54, also functions as a reactor plate and insures that the tortuous path is not circumvented. Interior to the outer reactor plate is at least one intermediate reactor plate, 56, which is a truncated cylinder. The truncation of the intermediate reactor plate is opposite to the first truncation, 52, of the first reactor plate. This insures that flow is around the plate thereby forcing a serpentine pattern of flow. An inner reactor plate, 58, is a twice truncated cylinder wherein one truncation is open and opposite to the truncation of the closest intermediate reactor plate thereby insuring serpentine flow. The other truncation is attached to the flow restrictor walls, 54. The area interior to the inner reactor plate and flow restrictor walls is referred to herein as the mixing region.

As would now be realized, the air flowing into the air inlet void, 22, contacts the interior of the flow restrictor walls and inner reactor plates. The air then exits the open truncation of the inner reaction plate and traverses between the inner reactor plate and intermediate reactor plate until the truncation of the intermediate reactor plate is reached at which point it will traverse between the intermediate reactor plate and outer reactor plate until the open truncation, 52, of the outer reactor plate is reached at which point it must traverse around the outside of the outer reactor plate to ultimately reach the air outlet voids, 26. As will be realized, the air flowing in the tortuous path contacts the moist surface of the reactor plates which contains a bioreactor which is continuously wetted during operation.

The liquid medium flow in the reservoir is generally transverse to the flow of air in one embodiment. The air flow could be reversed without detriment. The liquid is pumped upward from the bottom of the inner workings ultimately exiting a water exit void, 60, with a dam there around as illustrated in FIG. 6. A deflector, 20, which is illustrated in FIGS. 2 and 3, covers the exit void and diverts the water onto the face, 34, of the cap, 18. As discussed above, the water then pools on the face and flows downward through the water voids, 30. The liquid voids are preferably arranged in concentric rings with each ring disposed above a reactor plate to allow liquid passing through the liquid void to bath the reactor plates with liquid thereby forming a liquid curtain which minimizes air from exiting the tortuous path and keeps the bioreactor moist. Any impurities brought in with the air will therefore react with the bioreactor, 90, on the moist surfaces of the reactor plates primarily above the surface of the liquid.

Starting from the reservoir, the liquid flow is upward from the bottom of the inner workings to the face of the cap. Starting from the furthest extent for completeness, the liquid flows down the wall until it is reunited with the bulk of the liquid forming a reservoir in the bottom of the tub. The liquid in the reservoir then traverses around the outside of the outer reactor plate until it reaches the open truncation therein. The liquid then transits between the outer reactor plate and intermediate reactor plate. The liquid is then directed by the flow restrictor walls through the truncation of the intermediate reactor plate where it flows between the intermediate reactor plate and inner reactor plate until it reaches the open truncation of the inner reactor plate at which point it is in position to flow towards the pump to traverse back to the face of the cap. Alternatively, holes in the reactor plates can be utilized below the level of the liquid to minimize the flow length.

An embodiment of the invention will be described with reference to FIG. 7 wherein the reactor plates are illustrated in isolated schematic top view. The outer reactor plates, 50, intermediate reactor plates, 56, inner reactor plates, 58, and flow restrictor walls, 54, are as discussed above. Each truncation, with reference to 52, is independently defined by an angle, $\alpha$, which is the angle of the cylinder which is absent. As would be realized, the larger the angle the less surface area is available for bioreactor to reside on. In the embodiment of FIG. 7, arcuate secondary reactor plates, 70, are disposed in the spaces between the outer reactor plate and intermediate reactor plate and in the space between the intermediate reactor plate and inner reactor plate. The secondary reactor plates are twice truncated cylinders. It is preferred that the truncated portion of the secondary reactor plate, which is aligned with a truncated portion of an adjacent reactor plate, has a larger angle of truncation than the adjacent reactor plate. For example, the open truncation of the outer reactor plate, 52, has an angle of truncation represented by the angle, $\alpha$. The truncated portion of the outer secondary reactor plate has a preferred truncation, $\beta$, wherein $\beta$ is larger than $\alpha$, and inclusive of, the angle, $\alpha$. It is preferred that the truncated portion of the secondary reactor plates is symmetrical about the truncated portion of the adjacent reactor plates. By way of example, $\alpha$ and $\beta$ are preferably both symmetrical about line 71. The secondary reactor plates provide an increased surface area with minimal back pressure. As would be apparent the cap would preferably contain liquid voids disposed above the secondary reactor plate to insure that they remain moist.

The reactor plates are preferably cylindrical as described herein and most preferably the reactor plates are truncated cylinders. For the purposes of the present invention a cylinder is defined as the surface traced by a straight line moving at a fixed angle, and preferably parallel, to a fixed line and intersecting a fixed planar closed curved. The closed curve is preferably selected from oval, round and obround with round being most preferred. The separation between semi-curves forming related reactor plates is preferably about the diameter of the truncated cylinder. By way of example, and with reference to FIG. 5, the outer reactor plates preferably represent two semicurves which correspond to portions of a common truncated cylinder. The separation of the outer reactor plates is preferably no more than the diameter of the common truncated cylinder. The separation can be less than the diameter of the common truncated cylinder with the proviso that the flow does not approach linear. In practice, the separation of related reactor plates is preferably no more than 25% less than the diameter of the common truncated cylinder.

An embodiment of a truncated cylinder is illustrated in FIG. 9. The truncated cylinder, 100, is represented with a single truncation, 101, for illustrative purposes with the understanding that a second truncation could be the same or different. The truncation, 101, is asymmetrical vertically with a larger void area towards the lower portion of the cylinder. The truncation may be a partial truncation with a portion untruncated as illustrated in FIG. 9. This asymmetrical truncation allows variable linear flow velocity which causes disturbances away from linear flow and can, for example, assure desirable airflow along the lower portions of the reactor plates and along the surface of the liquid reservoir. As would be realized from the discussion herein flow disturbances, particularly in the air flow, increases the interaction between air born contaminants and the moist interior surfaces of the air purifier.

Cylindrical reactor plates with a consistent radius are desired due to manufacturing simplicity. Related shapes such as oval cylinders and obround cylinders can be employed to demonstrate the invention but these are less desirable due to manufacturing complexities.

The reaction plates are preferably corrugated with corrugations being perpendicular to the axis of the cylinder. The corrugations increase the surface area of the reactor plates. The corrugations may be sinusoidal or truncated sinusoidal with flattened peaks and or valleys. It is preferred that the reaction plate is a solid with the inner and outer faces being parallel, however, the inner and outer faces may have different patterns or at least one of the surfaces can be smooth.

The liquid, or medium, is not particularly limited herein with the proviso that it must be compatible with the biocatalyst. Typical liquids include lower molecular weight organic materials and water. Water is the most preferred.

An embodiment of the invention will be described with reference to FIG. 8. In FIG. 8 the cap, 18, is illustrated as a separate component which mates with the top of the tub and which can be separated from the tub. It would be within the scope of the invention to have a tube which has a cap, or some portion of the cap, integral thereto but separate components are preferable for convenience in manufacturing, assembly, disassembly, repair and recharge. The cap is preferably attached in such a manner as to restrict or minimize the air from escaping the tortuous path. The pump, 80, draws liquid from the lower portion of the tub and discharges the liquid above the face, 34, wherein it is spread over the face by the preferred deflector, 20. The deflector is illustrated as a separate element but the deflector could be in integral part of the cap or the pump. The deflector functions to distribute liquid over the face, preferably with minimal splashing and noise, but this function could be achieved with other mechanisms. A preferred shut-off float, 81, provides protection from low water. If the water is below a predetermined level the shut-off float stops the pump thereby insuring against possible detrimental impact associated with low water. The shut-off float may be mechanical or electrical interruption of the pumping mechanism with electrical being preferred due to the simplicity offered there by. The shut-off float may be integral to the pump or it may be an auxiliary component in controlling relationship with the pump through electrical, mechanical or intermediate means such as a control component. A fan, 92, pulls contaminated air through the air grid, 12, wherein the contaminated air passes through the tortuous path and contacts the moist reactor plates wherein contaminants react with the bioreactor on the moist reactor plates.

Figure 10:
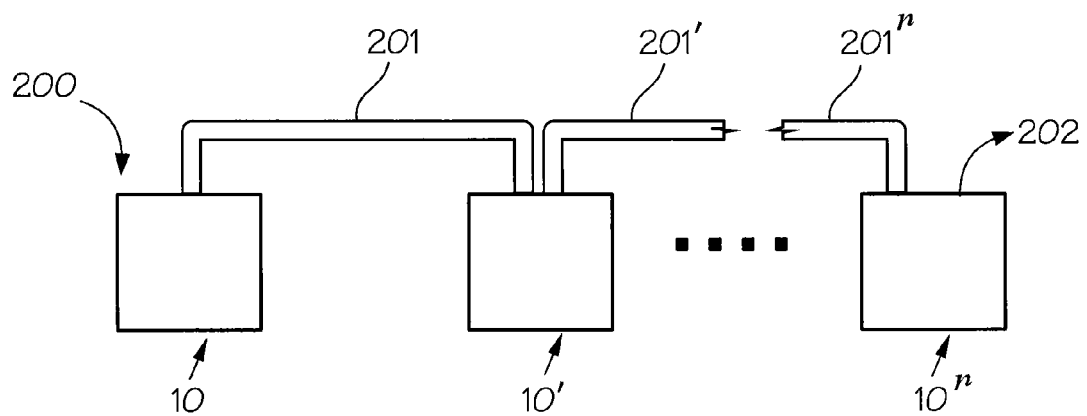
FIG. 10 is a schematic view of an embodiment of the invention.

An embodiment of the invention is illustrated in FIG. 10. In FIG. 10 a multiplicity of air purifiers are combined in series. A first air purifier, 10, receives incoming contaminated air at 200. The contaminated air is at least partially purified in the first air purifier and discharged into a duct, 201, which supplies air to the second air purifier, 10'. Each air purifier receives air from a previous air purifier and discharges to a subsequent air purifier until the final air purifier, 10", where it is discharged as purified air at 202.

In use, the bioreactor is charged with an immobilized biocatalyst such as an enzyme. The biocatalyst adheres to any surface within the bioreactor which is in a wet environment. As understood by one of skill in the art the biocatalyst may grow, or multiply, depending on the type of biocatalyst.

While not limited thereto, the preferred reactant is a biocatalyst. The biocatalyst may be aerobic or anaerobic with particularly preferred biocatalyst selected from the group consisting of enzymes, bacteria, organelles, leucocytes, hemocytes, yeast, fungi, similar materials or their products. A particularly preferred biocatalyst is an enzyme with BioOx® Enzymes available from sgblue inc. of Arden, N.C. being most preferred.

The reaction system preferably includes oxidation, either alone or in combination with other reactive systems such as anaerobic digestion, fermentation, immune reactions, blood cell or tissue cell reactions, enzyme reactions, organelle reactions or ordinary chemical reactions. A particularly preferred reaction system is a self-immobilization catalyst which is a biocatalyst immobilized on the interior walls of the bioreactor in a proteinaceous preparation.

The invention has been described with reference to the preferred embodiments without limit thereto. One of skill in the art would realize additional embodiments and improvements which are not specifically stated but are within the scope of the claims appended hereto.

The invention claimed is:

1. An air purifier comprising:
   a tub capable of containing a liquid;
   flow restrictor walls in said tub;
   an outer arcuate reactor plate in said tub wherein said outer arcuate reactor plate comprises a first truncated cylinder with a first truncation and a second truncation wherein said first truncation is an open truncation and said second truncation is attached to said flow restrictor walls;
   an intermediate arcuate reactor plate interior to said outer arcuate reactor plate wherein said intermediate arcuate reactor plate comprises a second truncated cylinder;
   an interior arcuate reactor plate interior to said intermediate arcuate reactor plate wherein said interior arcuate reactor plate comprises a third truncated cylinder comprising a third truncation and a fourth truncation wherein said third truncation is an open truncation and said fourth truncation is attached to said flow restrictor walls;
   a pump situated to draw said liquid from a region formed by said interior arcuate reactor plate and said flow restrictor walls for distribution onto a cap;
   said cap on said tub wherein said cap comprises liquid voids wherein said liquid passes through said liquid voids and wets at least one of said outer arcuate reactor plate, said intermediate arcuate reactor plate, said interior arcuate reactor plate or said flow restrictor walls to form a moist surface;
   an air inlet for bringing contaminated air into contact with biocatalyst on at least one said moist surface thereby forming purified air; and
   an air outlet for discharging said purified air from said air purifier.

2. The air purifier of claim 1 wherein said moist Surface is selected from at least one of said outer arcuate Reactor plate, said intermediate arcuate reactor plate and said inner arcuate reactor plate.

3. The air purifier of claim 2 wherein said biocatalyst is a self-immobilization catalyst.

4. The air purifier of claim 1 further comprising an external casing with said tub therein.

5. The air purifier of claim 4 further comprising an air grid attached to said external casing.

6. The air purifier of claim 1 further comprising a deflector.

7. The air purifier of claim 6 wherein said deflector is on said cap.

8. The air purifier of claim 1 wherein said liquid voids are arranged such that liquid flowing through said liquid voids flows directly onto said at least one of said outer arcuate reactor plate, said intermediate arcuate reactor plate and said interior arcuate reactor plate.

9. The air purifier of claim 1 wherein said cap further comprises air passages.

10. The air purifier of claim 9 wherein said cap further comprises dams around said air passages.

11. The air purifier of claim 10 wherein said dams form a reservoir on said cap.

12. The air purifier of claim 1 wherein portions of said outer arcuate reactor plate are separated by a distance which is no more than a diameter of said first truncated cylinder.

13. The air purifier of claim 1 wherein portions of said intermediate arcuate reactor plate are separated by a distance which is no more than a diameter of said second truncated cylinder.

14. The air purifier of claim 1 wherein portions of said interior arcuate reactor plate are separated by a distance which is no more than a diameter of said third truncated cylinder.

15. The air purifier of claim 1 further comprising at least one secondary reactor plate.

16. The air purifier of claim 15 wherein said secondary reactor plate is in at least one location selected from between said outer arcuate reactor plate and said intermediate arcuate reactor plate or between said intermediate arcuate reactor plate and said interior arcuate reactor plate.

17. The air purifier of claim 15 wherein said secondary reactor plate is a fourth truncated cylinder.

18. The air purifier of claim 17 wherein said fourth truncated cylinder has a truncated portion which has a truncation angle which is larger than a truncation angle of an adjacent arcuate reaction plate.

19. The air purifier of claim 1 wherein at least one arcuate reactor plate comprises an asymmetrically truncated cylinder.

20. An air purifier system comprising a first air purifier and a second air purifier according to claim 1 wherein said second air purifier receives said purified air from said first air purifier and said second air purifier exhaust purified air.

21. A method of purifying air comprising:
A) providing an air purifier comprising:
   a tub capable of containing a liquid;
   flow restrictor walls in said tub;
   an outer arcuate reactor plate in said tub wherein
      said outer arcuate reactor plate comprises a first truncated cylinder with a first truncation and a second truncation, wherein said first truncation is an open truncation and said second truncation is attached to said flow restrictor walls;
   an intermediate arcuate reactor plate interior to said outer arcuate reactor plate, wherein said intermediate arcuate reactor plate comprises a second truncated cylinder;
   an interior arcuate reactor plate interior to said intermediate arcuate reactor plate,
wherein said interior arcuate reactor plate comprises a third truncated cylinder comprising a third truncation and a fourth truncation wherein said third truncation is an open truncation and said fourth truncation is attached to said flow restrictor walls;
   a pump situated to draw said liquid from a region formed by said interior arcuate reactor plate and said flow restrictor walls for distribution onto a cap; said cap positioned on said tub, wherein said cap comprises liquid voids wherein said liquid passes through said liquid voids and wets said at least one of said outer arcuate reactor plate, said intermediate arcuate reactor plate or said interior arcuate reactor plate;
   an air inlet for bringing contaminated air into contact with moist biocatalyst on at least one moist surface thereby forming purified air; and
   an air outlet for discharging said purified air from said air purifier;
B) providing a biocatalyst in a liquid;
C) inserting said liquid it said tub;
D) drawing air comprising a contaminant into said air purifier wherein
said contaminant reacts with said biocatalyst;
E) allowing said contaminant to react with said biocatalyst thereby forming an inert material; and
F) exhausting purified air from said air purifier.

22. The method of purifying air of claim 21 wherein said liquid is water.

23. The method of purifying air of claim 21 wherein said biocatalyst is a self-immobilization catalyst.

24. The method of purifying air of claim 21, wherein the air purifier further comprises at least one secondary reactor plate.

25. The method of purifying air of claim 24 wherein said secondary reactor plate is in at least one location selected from between said outer arcuate reactor plate and said intermediate arcuate reactor plate or between said intermediate arcuate reactor plate and said interior arcuate reactor plate.

26. The method of purifying air of claim 21 wherein said biocatalyst adheres to an interior surface of said air purifier.

27. The method of purifying air of claim 21 further comprising pumping said liquid from a mixing region formed by said interior arcuate reactor plate and said flow restrictor walls for distribution onto said cap.

* * * * *